US012139636B2

(12) United States Patent
Chlandová et al.

(10) Patent No.: US 12,139,636 B2
(45) Date of Patent: Nov. 12, 2024

(54) COMPOUND FOR SURFACE PROTECTION

(71) Applicant: FIRST POINT A.S., Hodonin (CZ)

(72) Inventors: Gabriela Chlandová, Borohrádek (CZ); Petr Španiel, České Meziřiči (CZ)

(73) Assignee: First Point A.S., Hodonin (CZ)

( * ) Notice: Subject to any disclaimer, the term of this patent is extended or adjusted under 35 U.S.C. 154(b) by 495 days.

(21) Appl. No.: 17/624,841

(22) PCT Filed: May 26, 2020

(86) PCT No.: PCT/CZ2020/000020
§ 371 (c)(1),
(2) Date: Jan. 4, 2022

(87) PCT Pub. No.: WO2021/004557
PCT Pub. Date: Jan. 14, 2021

(65) Prior Publication Data
US 2022/0267613 A1    Aug. 25, 2022

(30) Foreign Application Priority Data
Jul. 5, 2019  (CS) .................................. CZ2019-447

(51) Int. Cl.
| C09D 5/14 | (2006.01) |
| B27K 3/20 | (2006.01) |
| C01B 33/32 | (2006.01) |
| C07C 211/09 | (2006.01) |
| C09C 1/48 | (2006.01) |
| C09D 1/04 | (2006.01) |
| C09D 5/18 | (2006.01) |

(52) U.S. Cl.
CPC ............... *C09D 5/14* (2013.01); *B27K 3/20* (2013.01); *C01B 33/32* (2013.01); *C07C 211/09* (2013.01); *C09C 1/48* (2013.01); *C09D 1/04* (2013.01); *C09D 5/18* (2013.01); *B27K 2240/30* (2013.01); *B27K 2240/70* (2013.01)

(58) Field of Classification Search
CPC ... C09D 5/14; C09D 1/04; C09D 5/18; C09D 5/00; B27K 3/20; B27K 2240/30; B27K 2240/70; B27K 3/32; B27K 3/18; B27K 3/26; C01B 33/32; C07C 211/09; C09C 1/48; D06M 11/79; D06M 11/45; D06M 11/74; D06M 16/00; D06M 2200/30; C08J 7/05; C08J 2300/00; C08L 101/00; D21H 17/07; D21H 17/675; D21H 17/68; D21H 21/14; D21H 21/36; C09K 21/02
See application file for complete search history.

(56) References Cited

U.S. PATENT DOCUMENTS

2002/0009622 A1   1/2002   Goodson

FOREIGN PATENT DOCUMENTS

| CN | 101386719 A | 3/2009 | |
| CN | 104099060 B | 7/2015 | |
| CN | 109321074 A | 2/2019 | |
| CN | 109532154 A | 3/2019 | |
| CS | 30925 | 12/1929 | |
| CS | 111175 B | 6/1964 | |
| CS | 123593 B | 7/1967 | |
| CS | 175548 B1 | 12/1978 | |
| CS | 275550 B2 | 2/1992 | |
| CZ | 111175 B | 6/1964 | |
| CZ | 221191 A3 | 2/1993 | |
| CZ | 2000245 A3 | 6/2000 | |
| CZ | 20002127 A3 | 11/2001 | |
| CZ | 30925 U1 | 8/2017 | |
| CZ | 31269 U1 | 12/2017 | |
| CZ | 31596 U1 | 3/2018 | |
| EP | 1013726 A1 | 6/2000 | |
| JP | S56161477 A | 12/1981 | |
| JP | H08157315 A | 6/1996 | |
| JP | H10139568 A | 5/1998 | |
| JP | 2001072480 A | 3/2001 | |
| JP | 4021204 B2 * | 12/2007 | ............... B32B 9/00 |
| KR | 100820276 B1 | 4/2008 | |
| KR | 101905682 B | 10/2018 | |
| RU | 2544854 C1 | 3/2015 | |
| UA | 92979 C2 | 12/2010 | |
| WO | 2008066319 A1 | 6/2008 | |

OTHER PUBLICATIONS

U.S. Appl. No. 17/624,841 filed Jan. 4, 2022, Ms. Gabriela Chlandová.
U.S. Appl. No. 17/625,090 filed Jan. 15, 2022, Ms. Gabriela Chlandová.
U.S. Appl. No. 17/627,657 filed Jan. 15, 2022, Ms. Gabriela Chlandová.
Abstract for JPH10139568A listed in Database WPI, Week 199831, Thompson Scientific, London, GB7, Database accession No. AN1998-356334, XP002800042, [1998].
International Search Report for PCT/CZ2020/000020, [2020].
International Search Report for PCT/CZ2020/000024 [2020].
International Search Report for PCT/CZ2020/000025, [2020].
Search Report for Priority Application PV 2019-447, [2020].
Search Report for Priority Application PV 2019-449, [2019].
Search Report for Priority Application PV 2019-508, [2020].
Written Opinion for PCT/CZ2020/000020.
Written Opinion for PCT/CZ2020/000024.
Written Opinion for PCT/CZ2020/000025.

* cited by examiner

*Primary Examiner* — Anthony J Green
(74) *Attorney, Agent, or Firm* — Austin LLP

(57) ABSTRACT

A surface protection compound, in particular a compound for the non-flammable water-resistant non-hazardous biocidal surface protection of wood, or paper, or textile, or plastic, which contains an aqueous silicate solution which contains 93 to 98 wt % of an aqueous solution of potassium silicate, 1 to 6 wt % of aluminium hydroxide and, 0.5 to 1.5 wt % of stabiliser of the aqueous solution of potassium silicate.

6 Claims, No Drawings

COMPOUND FOR SURFACE PROTECTION

CROSS-REFERENCE TO RELATED APPLICATIONS

This application is a U.S. National Stage under 35 U.S.C. § 371 of International Application No. PCT/CZ2020/000020, as filed on May 26, 2020, which claims priority to the Czech Republic patent application No. PV 2019-447 filed on Jul. 5, 2019 and entitled "Compound for Surface Protection." The disclosure of each of these applications is incorporated by reference herein for all purposes.

TECHNICAL FIELD

The invention relates to a compound for surface protection, in particular a compound for the non-flammable water-resistant non-hazardous biocidal surface protection of wood, or paper, or textile, or plastic, which contains an aqueous solution of silicate.

STATE OF THE ART

From current technology numerous coatings for wood protection are known, which differ in relation to the intended use of the composition. The simplest compounds are in coatings only for finishing the surface of wood, which protects only against mechanical and chemical influences, and serves for decorative beautification. Higher quality coatings also protect against atmospheric influences, water, UV radiation, etc. Coatings that provide comprehensive wood protection also contain additional special additives, such as biocides, UV absorbers, flame retardants, etc. The amount of pigment in the coating also plays a large role in the amount of radiation transmitted, causing yellowing and browning of the wood and, together with the effect of water, greying.

From patent document KR101905682 a self-extinguishing compound for wood is known, which contains sodium diphosphate, urea, phosphoric acid, and borax. These substances are soluble in water, while the disadvantage is the possibility of washing the wood coating with water, the corrosive effect on surrounding metallic materials or even the wood itself, toxicity, relatively low efficiency and limited service life and difficult restoration.

From utility model UA92979 is known a mixture which contains ammonium hydrogen phosphate, ammonium sulphate and sodium fluoride. The substances are again soluble in water and therefore have the same disadvantages as the previous compound.

From patent document CS111175 is known a wood coating based on polyacrylate dispersions which has antiseptic effects. Its great disadvantage is that it is flammable.

Flammable is also the wood coating known from patent document CS123593. This coating is intended to be against moulds, fungi, and is based on chloronaphthalene.

From the aforementioned current technology it is clear that main disadvantage of current technology is that although there are fire retardant agents and agents with effects against other possible wood damage, such as mould or fungus, there is no agent which could combine these two properties.

The object of the invention is the composition of a compound for the fire protection of wood, which will also be its non-hazardous biocidal surface protection, and which will have the same protective properties for the protection of paper, or textiles, or plastics.

Principle of the Invention

The above-mentioned drawbacks are largely eliminated and the objects of the invention are fulfilled by a surface protection compound, in particular a compound for non-flammable water-resistant non-hazardous biocidal surface protection of wood or paper or textile or plastic, which contains an aqueous silicate solution which according to the invention is characterised by that it contains 93 to 98 wt % of an aqueous solution of potassium silicate, 1 to 6 wt % of aluminium hydroxide, 0.5 to 1.5 wt % of aqueous potassium silicate stabiliser. The advantage is that the surface treated with the compound has excellent fire resistance and at the same time excellent cytostatic properties. Another advantage is that the compound contains components of purely inorganic origin, which are harmless to the ecology and to health, and do not release any harmful gaseous, liquid or solid products during long-term exposure even in the event of fire and high temperature.

It is to advantage that the surface protection compound further comprises 1 to 3 wt % of an aqueous carbon black solution, while to greatest advantage the aqueous solution contains 25 wt % carbon black. The advantage of using carbon black in the compound is that the surface is not exposed to atmospheric oxygen and therefore they do not behave as a flammable particles, but on the contrary as a flame retardant. During combustion, they capture the emerging free radicals, which significantly slows down the burning. At the same time, they act as a carbonisation nucleator, trapping the resulting ash and thus accelerating the formation of a continuous carbon crust, which protects the wood surface from flame and at the same time reduces the content of the developing smoke, which consists of fly ash and carbon black.

It is to further great advantage if the aqueous potassium silicate solution has a density in the range from 1650 to 1670 $kg/m^3$ and the molar mass ratio of silicon oxide to potassium oxide is in the range from 1.67 to 1.73. At this advantageous concentration of the potassium silicate solution, excellent absorbency into the wood can be achieved, so that the depth of penetration of the compound into the wood is up to 6 mm.

Furthermore, it is also to advantage that the stabilisers of the aqueous potassium silicate solution are hydrophilic alkoxy alkyl-ammonium salts.

The main advantage of the compound according to the invention is that the surface treated with the compound has excellent fire resistance and at the same time excellent cytostatic properties. The compound also has excellent gluing and sealing effects, so that it perfectly wraps the wood fibres. After hardening, the surface is vapour-permeable, removing the initial residual moisture or moisture that may penetrate the wood. After hardening, the compound is also water-resistant and after application on perfectly dried wood, the volume of the object does not change. At the same time, the above brings excellent fungicidal properties, because the compound fills the porous substance of the wood and prevents the penetration of organisms into the wood. An advantageous property is also very good protection against UV radiation, which together with moisture causes the greying of wood. The created layer acts as a fire extinguisher even at a depth, where combustion does not take place and where it slows down all decomposition processes in the area of pyrolysis as well as below it. It also dampens the formation of gases that do not have free space in the wood to enter. A great advantage of the compound according to the invention is, at the same time, that absorbent plastics, such as foam, geo-textiles and felt, can be impregnated as well. The fabric treated in this way can be further wrapped, for example, in cabling or distribution pipes for cabling, which must be protected from fire. It is also advantageous that the compound-treated surface preserves the appearance of the wood and prevents colour changes due to degradation, and can be applied to all kinds of wooden elements and to wooden building elements and OSB panels.

EXAMPLES OF THE PERFORMANCE OF THE INVENTION

Example 1

The compound for non-flammable water-resistant non-hazardous biocidal surface protection of wood contains 93 wt % of aqueous potassium silicate solution, 6 wt % of aluminium hydroxide and, 1 wt % of stabiliser of the aqueous solution of potassium silicate.

The aqueous potassium silicate solution has a density of 1670 kg/m$^3$ and the molar mass ratio of silicon oxide to potassium oxide is 1.73.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is intended for non-flammable colourless wood impregnation.

Example 2

The compound for non-flammable water-resistant non-hazardous biocidal surface protection of wood contains 95 wt % of aqueous potassium silicate solution, 1 wt % of aluminium hydroxide, 1 wt % of stabiliser of the aqueous solution of potassium silicate and, 3 wt %. aqueous carbon black solution.

The aqueous potassium silicate solution has a density of 1650 kg/m$^3$ and the molar mass ratio of silicon oxide to potassium oxide is 1.67.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is intended for the non-combustible biocidal impregnation of wood.

Example 3

The compound for non-flammable water-resistant non-hazardous biocidal surface protection of wood, or paper, or textile, or plastic, contains 97 wt % of aqueous potassium silicate solution, 2 wt % of aluminium hydroxide and, 1 wt % of stabiliser of the aqueous solution of potassium silicate.

The aqueous potassium silicate solution has a density of 1655 kg/m$^3$ and the molar mass ratio of silicon oxide to potassium oxide is in the range of 1.70.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is specifically intended for non-flammable colourless biocidal colourless impregnation of paper products.

Example 4

The compound for non-flammable water-resistant non-hazardous biocidal surface protection of textiles or plastics contains 93 wt % of aqueous potassium silicate solution, 3 wt % of aluminium hydroxide, 1 wt % of stabiliser of the aqueous solution of potassium silicate and, 3 wt % aqueous carbon black solution.

The aqueous potassium silicate solution has a density of 1660 kg/m$^3$ and the molar mass ratio of silicon oxide to potassium oxide is 1.71.

The aqueous carbon black solution contains 25 wt % carbon black.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is intended for non-flammable impregnation of textiles and plastics.

Example 5

The compound for non-flammable water-resistant non-hazardous biocidal surface protection of textiles or plastics contains 97 wt % of aqueous potassium silicate solution, 1 wt % of aluminium hydroxide, 1 wt % of stabiliser of the aqueous solution of potassium silicate and, 1 wt % aqueous carbon black solution.

The aqueous potassium silicate solution has a density of 1650 kg/m$^3$ and the molar mass ratio of silicon oxide to potassium oxide is 1.69.

The aqueous carbon black solution contains 25 wt % carbon black.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is intended for non-flammable impregnation of textiles and plastics.

Example 6

The compound for non-flammable water-resistant non-hazardous biocidal surface protection of textiles or plastics contains 96 wt % of aqueous potassium silicate solution, 2 wt % of aluminium hydroxide, 1 wt % of stabiliser of the aqueous solution of potassium silicate and, 1 wt % aqueous carbon black solution.

The aqueous potassium silicate solution has a density of 1660 kg/m$^3$ and the molar mass ratio of silicon oxide to potassium oxide is 1.7.

The aqueous carbon black solution contains 25 wt % carbon black.

The stabilisers of the aqueous potassium silicate solution are hydrophilic alkoxy alkyl-ammonium salts, in the form of a 98% aqueous solution of N,N,N',N'-Tetrakis (2-hydroxypropyl) ethylenediamine.

The resulting compound is intended for non-flammable impregnation of textiles and plastics.

INDUSTRIAL APPLICATION

The surface protection compound according to the invention can be used particularly for the non-flammable water-resistant non-hazardous biocidal surface protection of wood, or paper, or textiles, or plastics, which can also be soft PUR foam, rubber or geo-textiles.

The invention claimed is:
1. A surface protection compound for the nonflammable water-resistant biocidal surface protection of wood, paper, textile, or plastic, comprising an aqueous silicate solution, comprising 93 to 98 wt % of an aqueous solution of potassium silicate, 1 to 6 wt % of aluminum hydroxide and, 0.5 to 1.5 wt % of stabilizer of the aqueous solution of potassium silicate.

2. The surface protection compound according to claim 1, further comprising 1 to 3 wt % aqueous carbon black solution.

3. The surface protection compound according to claim 1, wherein the aqueous potassium silicate solution has a density in the range of from 1650 to 1670 kg/m$^3$.

4. The surface protection compound according to claim 1, wherein the aqueous potassium silicate solution has a molar mass ratio of silicon oxide to potassium oxide in the range of from 1.67 to 1.73.

5. The surface protection compound according to claim 1, wherein the aqueous carbon black solution comprises 25 wt % carbon black.

6. The surface protection compound according to claim 1, wherein the stabilizers of the aqueous potassium silicate solution are hydrophilic alkoxy alkyl-ammonium salts.

* * * * *